US012702400B2

(12) United States Patent
Cunningham et al.

(10) Patent No.: US 12,702,400 B2
(45) Date of Patent: Aug. 11, 2026

(54) TISSUE REPAIR DEVICES AND METHODS OF USE

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Matthew D. Cunningham, Mansfield, MA (US); Geoffrey I. Karasic, Mansfield, MA (US); Miles Malone, Mansfield, MA (US); John A. Slusarz, Jr., Mansfield, MA (US); Han Teik Yeoh, Mansfield, MA (US); Paul Alexander Torrie, Andover, MA (US)

(73) Assignees: Smith & Nephew. Inc., Memphis, TN (US); Smith & Nephew Orthopaedics AG, Zug (CH); Smith & Nephew Asia Pacific Pte. Limited, Singapore (SG)

( * ) Notice: Subject to any disclaimer, the term of this patent is extended or adjusted under 35 U.S.C. 154(b) by 58 days.

(21) Appl. No.: 18/722,112

(22) PCT Filed: Dec. 14, 2022

(86) PCT No.: PCT/US2022/052897
§ 371 (c)(1),
(2) Date: Jun. 20, 2024

(87) PCT Pub. No.: WO2023/121935
PCT Pub. Date: Jun. 29, 2023

(65) Prior Publication Data

US 2025/0134513 A1 May 1, 2025

Related U.S. Application Data

(60) Provisional application No. 63/291,495, filed on Dec. 20, 2021.

(51) Int. Cl.
*A61B 17/04* (2006.01)
*A61F 2/08* (2006.01)

(52) U.S. Cl.
CPC ........ *A61B 17/0401* (2013.01); *A61F 2/0811* (2013.01); *A61B 2017/0404* (2013.01);
(Continued)

(58) Field of Classification Search
CPC .... A61B 2017/0414; A61B 2017/0404; A61B 2017/0409; A61B 17/06166; A61F 2002/0882
See application file for complete search history.

(56) References Cited

U.S. PATENT DOCUMENTS

| | | | | |
|---|---|---|---|---|
| 6,530,933 B1 * | 3/2003 | Yeung | A61B 17/083 606/151 |
| 2003/0130694 A1 * | 7/2003 | Bojarski | A61F 2/0811 606/228 |

(Continued)

FOREIGN PATENT DOCUMENTS

| | | |
|---|---|---|
| EP | 1568326 A1 | 8/2005 |
| EP | 3738519 A1 | 11/2020 |

(Continued)

OTHER PUBLICATIONS

International Search Report and Written Opinion issued in International Application No. PCT/US2022/052897 on Dec. 14, 2022.

*Primary Examiner* — Alexander J Orkin
(74) *Attorney, Agent, or Firm* — ArentFox Schiff LLP; Joseph M. Maraia

(57) ABSTRACT

Tissue repair devices described herein allow for meniscal root repair with sutures and anchors delivered by a needle. The needle houses two deployable anchors, each connected to a separate suture. The device also includes a push mechanism that allows for reliable anchor deployment through the needle. The needle can have various degrees of curvature to
(Continued)

access the superior or inferior surfaces of the meniscal roots. Each advancement of the push mechanism by the surgeon expels an individual suture/anchor construct from the distal tip of the needle at the desired location.

14 Claims, 11 Drawing Sheets

(52) U.S. Cl.
CPC ................. *A61B 2017/0409* (2013.01); *A61B 2017/0464* (2013.01); *A61F 2002/0882* (2013.01)

(56) References Cited

U.S. PATENT DOCUMENTS

2005/0187577 A1* 8/2005 Selvitelli ............ A61B 17/0401 606/232
2005/0192631 A1* 9/2005 Grafton ............ A61B 17/06166 606/228
2006/0178680 A1* 8/2006 Nelson ............... A61B 17/0467 606/139
2007/0083236 A1* 4/2007 Sikora ................ A61B 17/0401 606/232
2007/0270889 A1* 11/2007 Conlon ............. A61B 17/0487 606/232
2010/0130989 A1* 5/2010 Bourque ............ A61B 17/0482 606/144
2010/0160962 A1* 6/2010 Dreyfuss .......... A61B 17/06166 606/228
2011/0208239 A1* 8/2011 Stone ............... A61B 17/06004 606/228
2019/0090866 A1* 3/2019 Paterson ............... A61F 2/0811
2019/0365377 A1* 12/2019 Santangelo ........ A61B 17/0482
2020/0360007 A1* 11/2020 Cunningham ..... A61B 17/0401

FOREIGN PATENT DOCUMENTS

WO 01/39761 A1 6/2001
WO 2019/222439 A1 11/2019

* cited by examiner

TISSUE REPAIR DEVICES AND METHODS OF USE

CROSS-REFERENCE TO RELATED APPLICATIONS

This application is the U.S. national phase entry under 35 U.S.C. § 371 of International Application No. PCT/US2022/052897, filed Dec. 14, 2022, entitled TISSUE REPAIR DEVICES AND METHODS OF USE, which in turn claims priority to and benefit of U.S. Provisional Application No. 63/291,495, filed Dec. 20, 2021, the contents of which are incorporated herein by reference in their entirety for all purposes.

FIELD

The present disclosure relates to tissue repair devices and, more specifically, to tissue repair devices for performing meniscal root repair.

BACKGROUND

One of the most common forms of knee injury includes tearing of the meniscus, which often leads to pain, stiffness, and swelling in the knee joint. A meniscus root tear is usually either a separation of the meniscal root from its attachment point on the tibia or a tear within 1 cm of the root attachment. The integrity of the meniscal root attachment preserves correct knee function and avoids degenerative changes of the knee.

To perform a meniscal root repair, surgeons generally use a jawed suture passing device to both grasp the tissue and to place one or more sutures at the meniscal repair site. However, the jaws of these devices are often too large to safely grasp the tissue. Patient bone anatomy, as well as a "tight" knee, also often prevent the jaws from opening wide enough to grasp tissue. Damage to articular cartilage can also occur when using this type of device.

Another issue surgeons face with existing suture passing devices includes inaccurate placement of the suture, as the surgeon may find it difficult to visualize where the suture will exit the tissue. Moreover, the suture passed through the tissue may lacerate or elongate the disrupted tissue when the surgeon manipulates the suture. A surgeon must then use a simple stitch or "luggage tag" stitch to hold the suture to the tissue.

SUMMARY

Tissue repair devices described herein allow for meniscal root repair with sutures and anchors delivered by a needle rather than a jawed suture passer. The needle houses two deployable anchors, each connected to a separate suture. The device also includes a push mechanism that allows for reliable anchor deployment through the needle. The needle can have various degrees of curvature to access the superior or inferior surfaces of the meniscal roots. Each advancement of the push mechanism by the surgeon expels an individual suture/anchor construct from the distal tip of the needle at the desired location.

Further examples of the tissue repair devices and methods of use of this disclosure may include one or more of the following, in any suitable combination.

In examples, a tissue repair device of this disclosure includes a handle and an elongated needle defining a bore extending from the handle. The needle has a proximal end and a distal end. A first anchor and a second anchor are disposed at least partially within the bore of the needle. The second anchor is disposed proximal to the first anchor. Each of the first and second anchors are coupled, respectively, to a first flexible member and a second flexible member. The first flexible member is separate from the second flexible member.

In further examples, the tissue repair device also includes a knob at least partially disposed within the handle and a hub coupled to the handle. The hub including a flange for manually advancing the knob relative to the hub. In examples, the needle extends from the handle through an outer tube extending through the hub. In examples, a distal portion of the needle is curved relative to a proximal portion of the needle. In examples, an outer surface of the needle defines a slot extending from the outer surface to the bore and an upper surface of the first and second anchors projects above the slot. In examples, a curvature of the needle extends in-line with the slot. In examples, the needle further includes a beveled, tissue piercing tip. In examples, at least one of the first and second flexible members is made of suture or suture tape. In examples, the first flexible member has a round distal portion routed through the first anchor and a flat proximal portion extending from the round distal portion. In examples, the first anchor defines a U-shaped suture pathway through which the round distal portion of the first flexible member passes. The suture pathway begins and ends at a top surface of the first anchor. In examples, a free end of the first flexible member is routed through the suture pathway and then through a center of the first flexible member, creating a finger trap above the top surface of the first anchor. In examples, at least one of the first and second anchors comprises an elongate, generally cylindrical body and a rail extending from a top surface of the body. In examples, at least one end of the rail includes a beveled end sloped toward the top surface of the body. In examples, at least one of the first and second anchors has a symmetrical cross-section along both a length and width of the anchor.

Examples of a method of tissue repair of this disclosure include creating at least one bone tunnel through a bone extending toward a tear in tissue. A tissue repair device is inserted through the bone tunnel. The tissue repair device includes a handle and an elongated needle defining a bore extending from the handle. The needle has a proximal end and a distal end. A first anchor and a second anchor are disposed at least partially within the bore of the needle. The second anchor is disposed proximal to the first anchor. Each of the first and second anchors are coupled, respectively, to a first flexible member and a second flexible member. The first flexible member is separate from the second flexible member. The first anchor is deployed from the bore of the needle on a first side of the tear such that the first flexible member extends through the at least one bone tunnel to an outside surface of the bone.

In further examples, the second anchor is deployed from the bore of the needle on a second side of the tear such that the second flexible member extends through the at least one bone tunnel to an outside surface of the bone. In examples, free ends of the first and second flexible members are secured to the outside surface of the bone with a fixation device. In examples, the first flexible member has a round distal portion routed through the first anchor and a flat proximal portion extending from the round distal portion through the at least one bone tunnel.

Examples of another method of tissue repair of this disclosure include creating at least one bone tunnel through a bone extending toward a tear in tissue. A looped portion of a flexible member is passed through the tissue adjacent the tear. A free end of the flexible member is passed through the looped portion and the free end is tensioned such that the looped portion is secured to the tissue. The free end of the flexible member is passed through the at least one bone tunnel to an outside surface of the bone. In examples, the flexible member comprises a round distal portion forming the looped portion and a flat proximal portion extending from the round distal portion through the at least one bone tunnel.

A reading of the following detailed description and a review of the associated drawings will make apparent the advantages of these and other features. Both the foregoing general description and the following detailed description serve as an explanation only and do not restrict aspects of the disclosure as claimed.

BRIEF DESCRIPTION OF THE DRAWINGS

Reference to the detailed description, combined with the following figures, will make the disclosure more fully understood, wherein.

DETAILED DESCRIPTION

Figure 1:
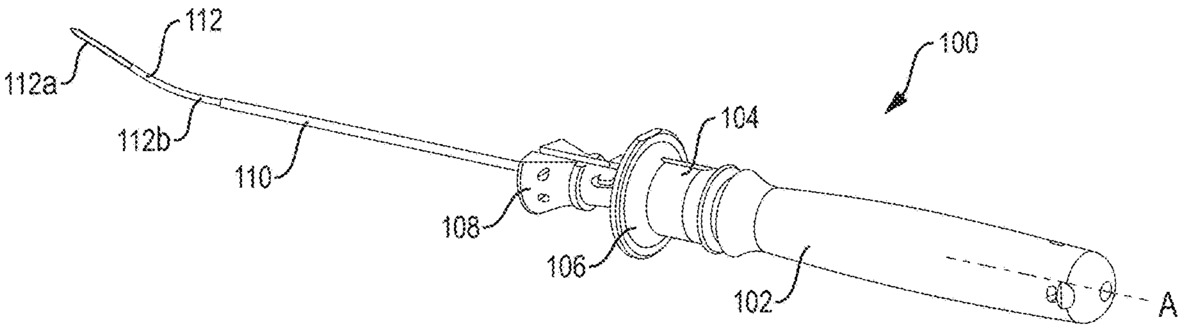
FIG. 1 shows an example of the tissue repair device of this disclosure in a perspective view.

In the following description, like components have the same reference numerals, regardless of different illustrated examples. To illustrate examples clearly and concisely, the drawings may not necessarily reflect appropriate scale and may have certain features shown in somewhat schematic form. The disclosure may describe and/or illustrate features in one example, and in the same way or in a similar way in one or more other examples, and/or combined with or instead of the features of the other examples.

In the specification and claims, for the purposes of describing and defining the invention, the terms "about" and "substantially" represent the inherent degree of uncertainty attributed to any quantitative comparison, value, measurement, or other representation. The terms "about" and "substantially" moreover represent the degree by which a quantitative representation may vary from a stated reference without resulting in a change in the basic function of the subject matter at issue. Open-ended terms, such as "comprise," "include," and/or plural forms of each, include the listed parts and can include additional parts not listed, while terms such as "and/or" include one or more of the listed parts and combinations of the listed parts. Use of the terms "top," "bottom," "above," "below" and the like helps only in the clear description of the disclosure and does not limit the structure, positioning and/or operation of the tissue repair device in any manner.

FIG. 1 shows an example of the tissue repair device 100 of the present disclosure. The tissue repair device 100 may generally include a handle 102 and a knob 104 at least partially disposed within the handle 102. A hub 108 may couple to the handle 102 distally of the knob 104. The knob 104 may include a flange 106 for manually advancing the knob 104 along a shared central axis A of the handle 102 and the hub 108. A needle 112 may extend from the handle 102 through an outer tube 110 extending through the hub 108. The needle 112 may be configured to house at least two anchors within an axial bore of the needle 112, as further described below. A push mechanism (not shown) may be disposed within the handle 102 and the needle 112 to successively deploy the anchors along a the axis A by advancement of the knob 104 relative to the hub 108. Non-limiting examples of the push mechanism are described in U.S. Pat. No. 8,888,798 to Smith & Nephew, Inc. (Memphis, TN), the entire contents of which are incorporated herein by reference. In examples, a distal portion 112*a* of the needle 112 may curve relative to a proximal portion 112*b* and the outer tube 110 to better enable placement of the anchors. The disclosure also contemplates that the needle 112 could have a pre-bent curvature (for example, a u-shaped hook, a corkscrew helix, etc.) to better enable anchor placement.

Figure 2:
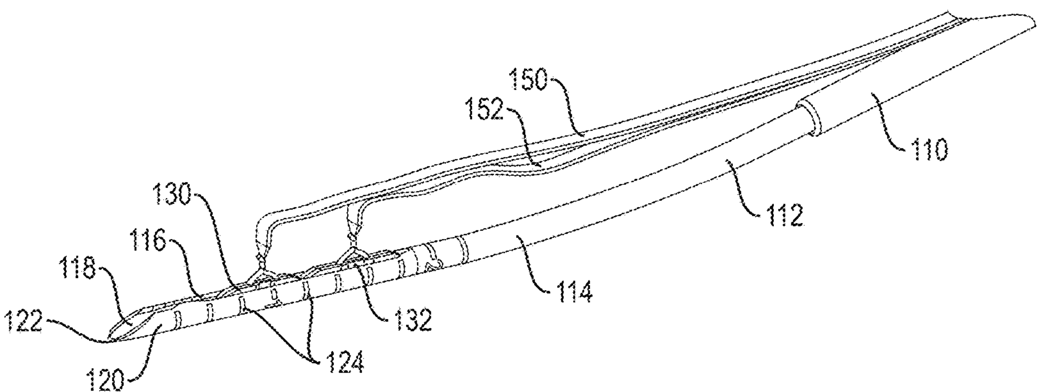
FIG. 2 shows a distal end of the needle of the device of FIG. 1.

FIG. 2 shows examples of a distal end of the needle 112 of this disclosure. As shown in FIG. 2, the needle 112 may define a slot 116 extending from an outer surface 114 to an axial bore 118 defined by the needle 112. A curvature of the needle 112 may extend in-line with the slot 116. The needle 112 may further include an open distal end 120 with a beveled, tissue piercing tip 122. The outer surface 114 of the needle 112 may further comprise markings 124 for coordination with a depth tube (not shown) in limiting the insertion depth of the needle 112. The axial bore 118 may be configured to house the anchors 130, 132 such that an upper surface of the anchors 130, 132 projects above the slot 116. The anchors 130, 132 may each couple to a separate flexible member, such as a suture 150, 152. The sutures 150, 152 in turn do not attach to each other.

Figure 3:
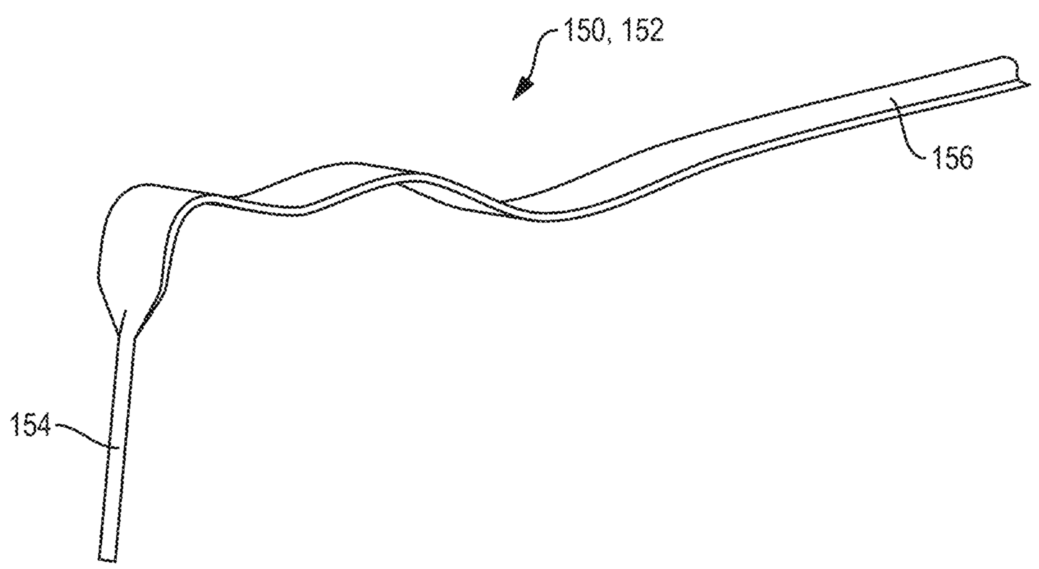
FIG. 3 shows an example of a suture for use with the device of FIG. 1.

FIG. 3 shows an example of the suture 150, 152, which may comprise monofilament, suture tape, or the like. The suture 150, 152 may include a round distal portion 154 and a flat proximal portion 156. The round distal portion 154 may advantageously facilitate attachment to the anchor 130, 132, as further described below. Meanwhile, the flat proximal portion 156 may beneficially impede laceration of the surrounding tissue when tensioned during the tissue repair. The disclosure also contemplates an entirely round suture 150, 152 having a distal diameter selected to be smaller than a proximal diameter. In examples, the suture 150, 152 may comprise a polymer material, including absorbable and non-absorbable polymer materials.

Figure 4A:
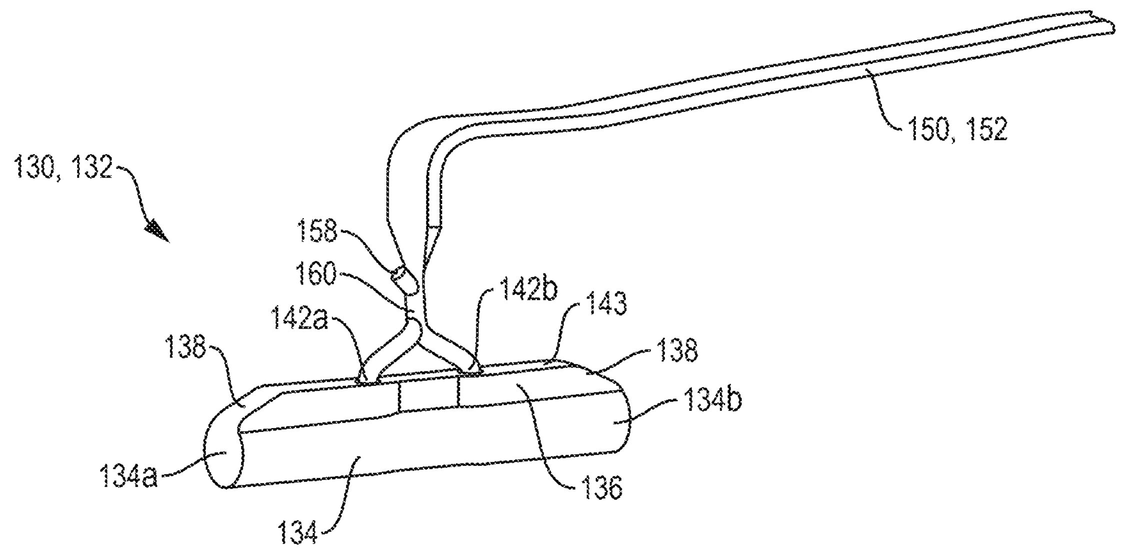
FIGS. 4A and 4B show examples of the suture of FIG. 3 routed through a suture pathway of an anchor.

FIG. 4A shows an example of the suture 150, 152 attached to the anchor 130, 132. In examples, the anchor 130, 132 may comprise rigid, biocompatible materials, such as polyethylene, an acetal, or polypropylene. Alternatively, the anchor 130, 132 may comprise metal, resiliently deformable materials (including all-suture materials), or bioabsorbable materials. Examples of the anchor 130, 132 can have various configurations, but may comprise a unitary, injection molded piece. In examples, the anchor 130, 132 may have an elongate, generally cylindrical body 134 dimensioned to conform to the cross-sectional area of the axial bore 118 of the needle 112 so that it forms a close sliding fit within the needle 112. The anchor 130, 132 may also have a rail 136 extending from a top surface of the body 134 from the distal end 134*a* to the proximal end 134*b* of the body 134. Each end of the rail 136 may include a beveled end 138 sloped toward the body 134. In examples, the anchor 130, 132 may have a symmetrical cross-section along both a length and width of the anchor 130, 132, which advantageously eliminates the possibility of accidentally loading the anchor 130, 132 backwards into the axial bore 118.

Figure 4B:
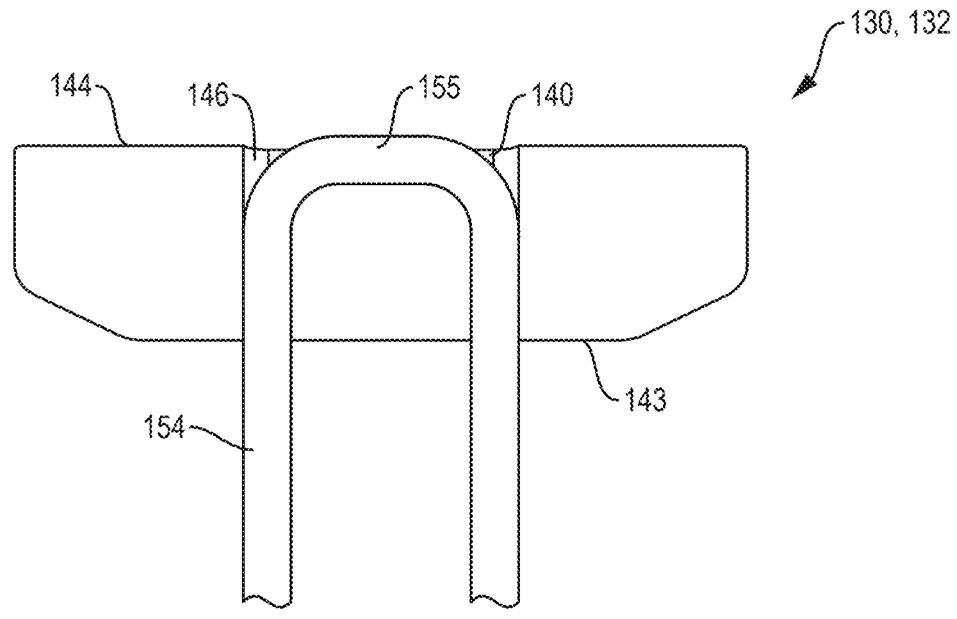

FIG. 4B shows an example of a cross-section of the anchor 130, 132. As shown in FIG. 4B, the anchor 130, 132 may define an internal suture pathway 140 through which the round distal portion 154 of the suture 150, 152 may pass. The suture pathway 140 may begin and end at a top surface 143 of the anchor 130, 132 at through holes 142*a*, 142*b* (FIG. 4A). The bottom surface 144 of the anchor 130, 132 may include a lengthwise recess 146 forming the bottom of a "U" shaped example of the suture pathway 140 through which a looped portion 155 of the suture 150, 152 passes. However, other configurations of the suture pathway 140 are contemplated by this disclosure. After routing through the suture pathway 140, the free end 158 of the suture 150, 152 that exits the through hole 142*a* may pass through the center of the suture 150, 152, creating a "finger trap" 160 above the top surface 143 of the anchor 130, 132 between the through holes 142*a*, 142*b*. The disclosure also contemplates other ways of securing the suture 150, 152 to the anchor 130, 132, such as a glued joint or a knot instead of the finger trap 160. The configuration of the suture pathway 140 advantageously results in positioning the finger trap 160 outside of the axial bore 118, so that the finger trap 160 does not interfere with the deployment of the anchor 130, 132.

Figure 5A:
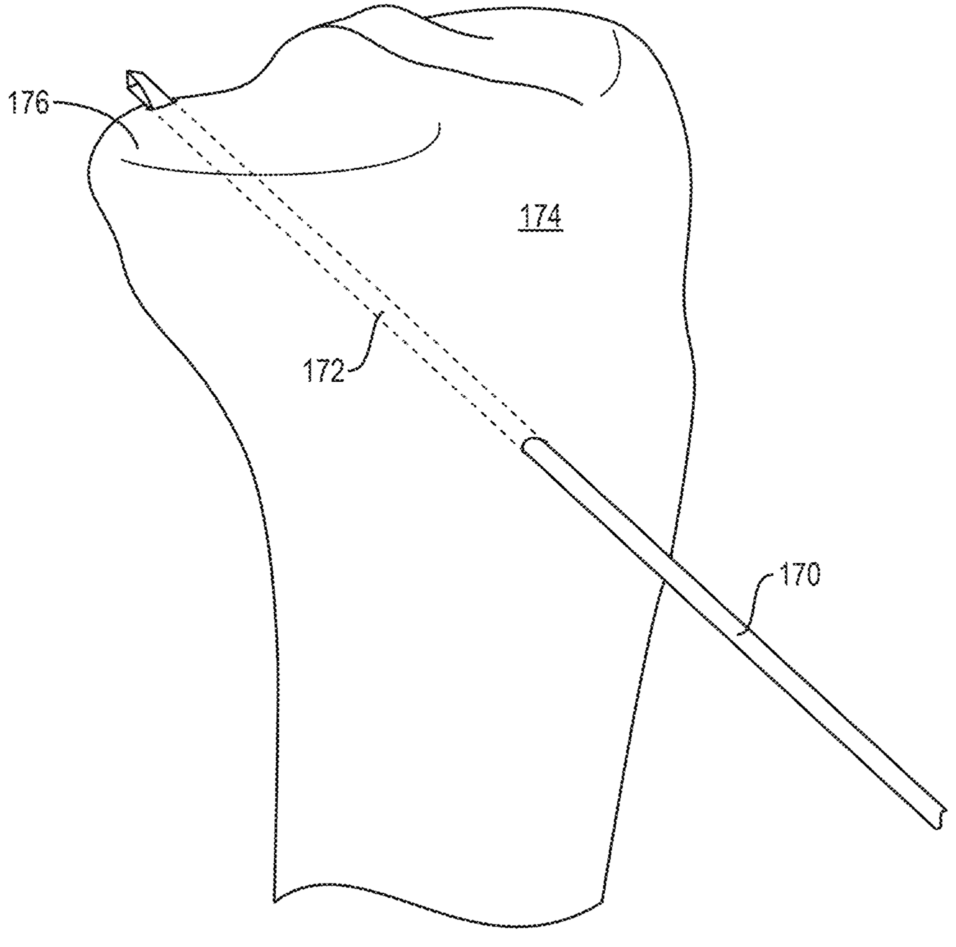
FIGS. 5A-E illustrate a method of using the device of FIG. 1 in a meniscal root repair.
Figure 5B:
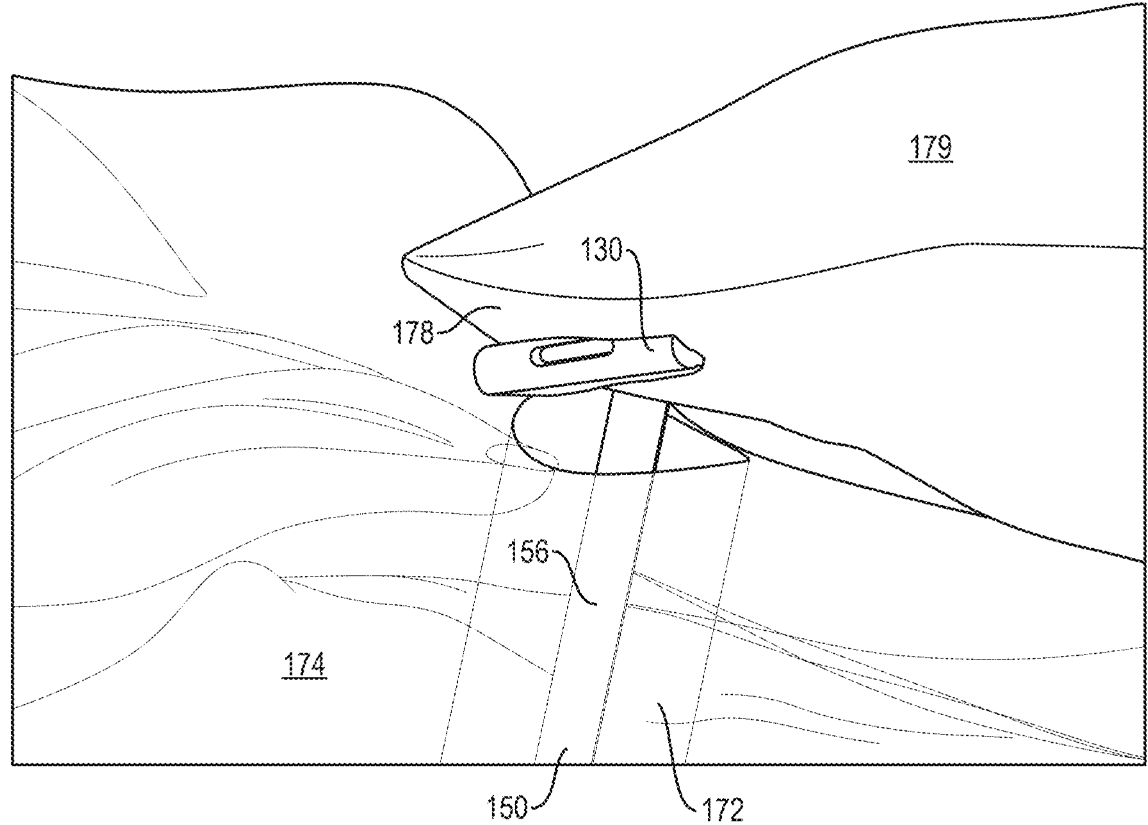
Figure 5C:
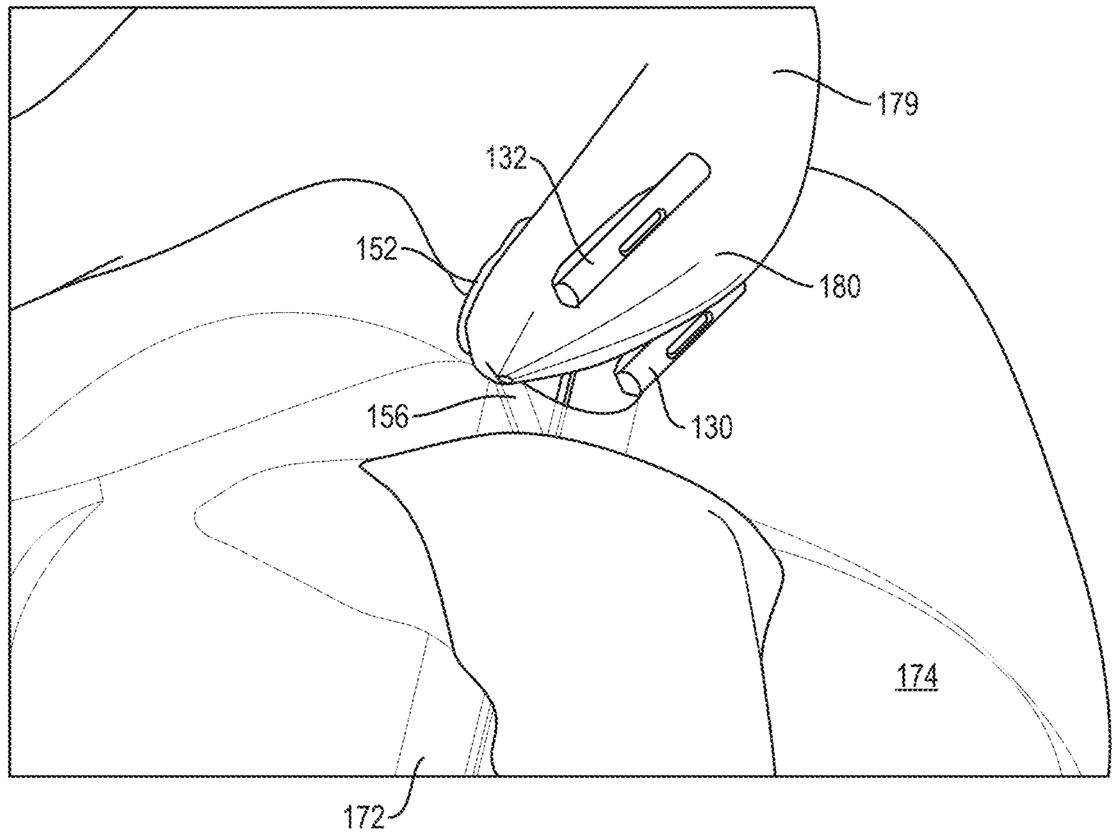

FIGS. 5A-E illustrate an example of a meniscal root repair using the tissue repair device 100 of FIG. 1. As shown in FIG. 5A, a surgeon may first use a curette or shaver blade (not shown) to prepare a bony bed, or decortication, of the tibial plateau 176 where the surgeon will perform the meniscus repair. Using a drill 170, the surgeon may then drill one or more bone tunnels 172 through the tibia 174 for passage of the needle 112 towards the meniscal root (not shown) at the tibial plateau 176. As shown in FIG. 5B, the surgeon may then use the tissue repair device 100 to deploy the anchor 130 from the needle 112 through the superior surface 178 of the meniscus 179 such that the flat proximal portion 156 of the suture 150 extends through the bone tunnel 172 to the outside surface of the tibia 174. As shown in FIG. 5C, the surgeon may then deploy the anchor 132 from the needle 112 through the inferior surface 180 of the meniscus 179 such that the flat proximal portion 156 of the suture 152 extends through the bone tunnel 172 to the outside surface of the tibia 174.

Figure 5D:
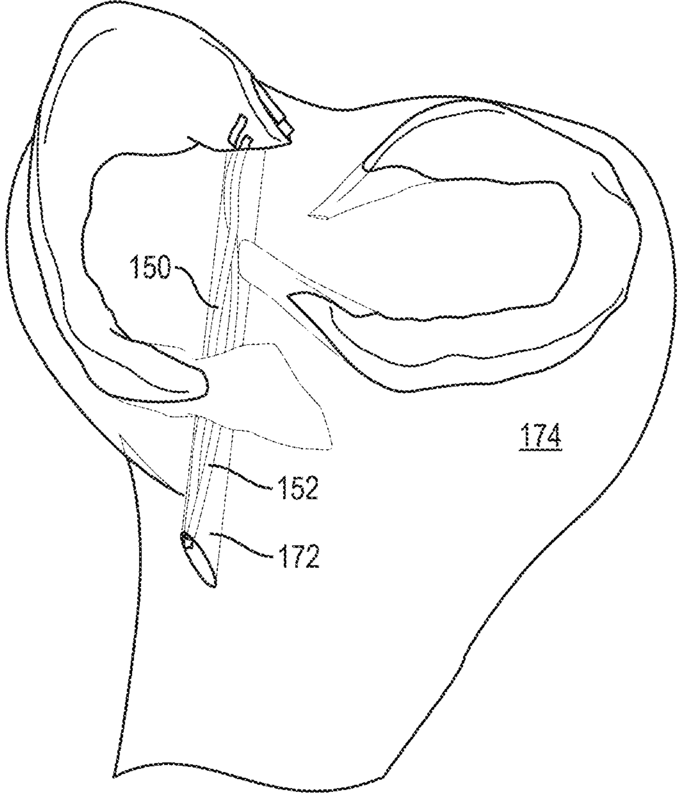
Figure 5E:
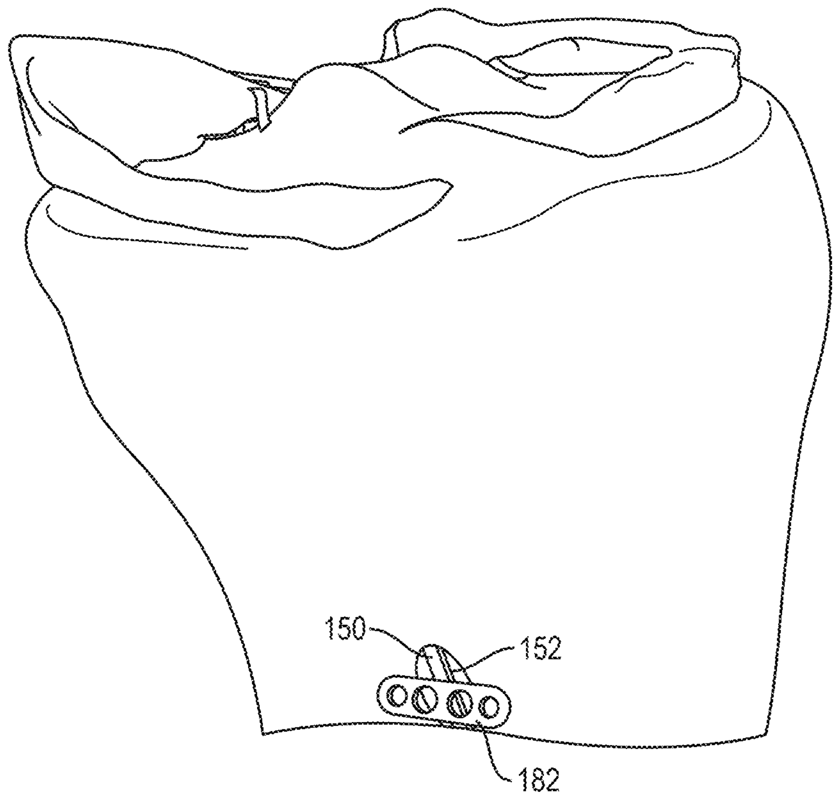

FIG. 5D shows both sutures 150, 152 extending through a single bone tunnel 172. However, the disclosure contemplates that the sutures 150, 152 could each extend through a separate bone tunnel through the tibia 174. Finally, as shown in FIG. 5E, the surgeon may then secure the sutures 150, 152 to an outer surface of the tibia 174 using a fixation device 182. Examples of the fixation device 182 may be a flat, oval-shaped button, as shown. However, the disclosure also contemplates other fixation devices, such as a round button or a spiked plate, and other means of fixation, such as to an interior surface of the bone tunnel 172.

Figure 6A:
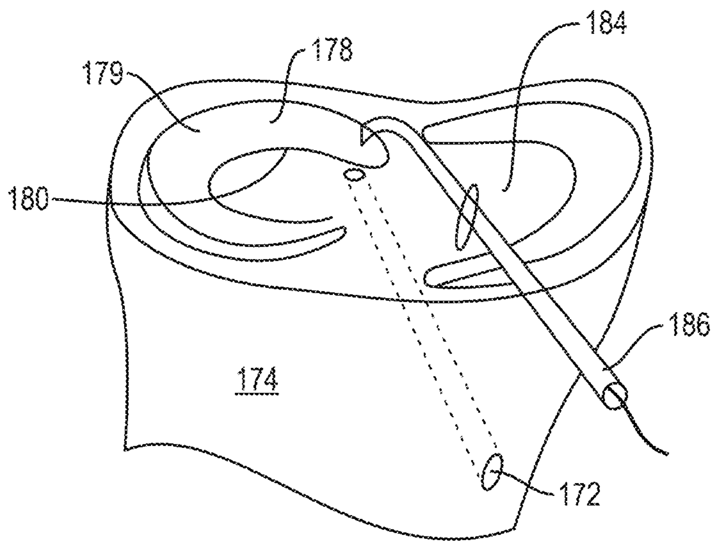
FIGS. 6A-F illustrate an alternative method of performing a meniscal root repair without the use of the anchors.
Figure 6B:
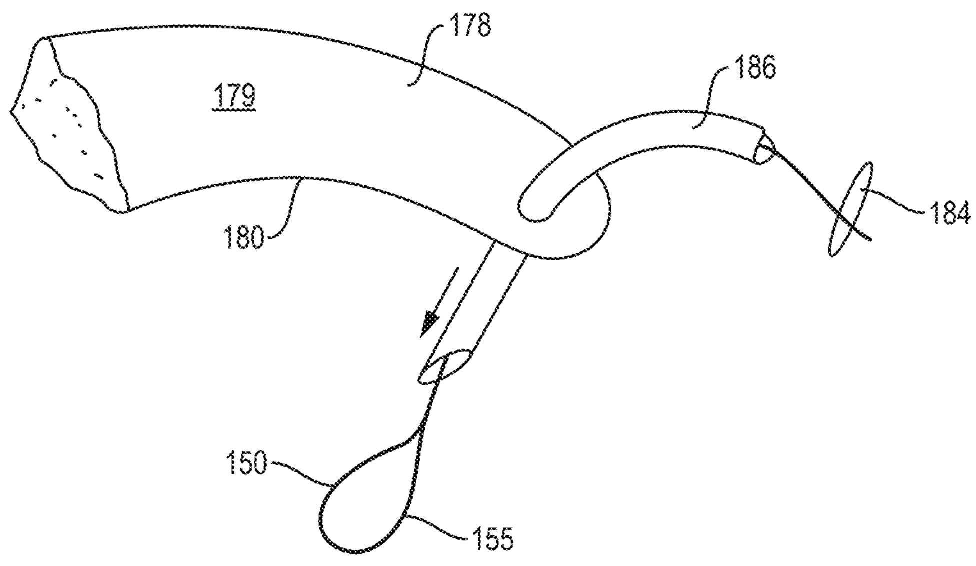
Figure 6C:
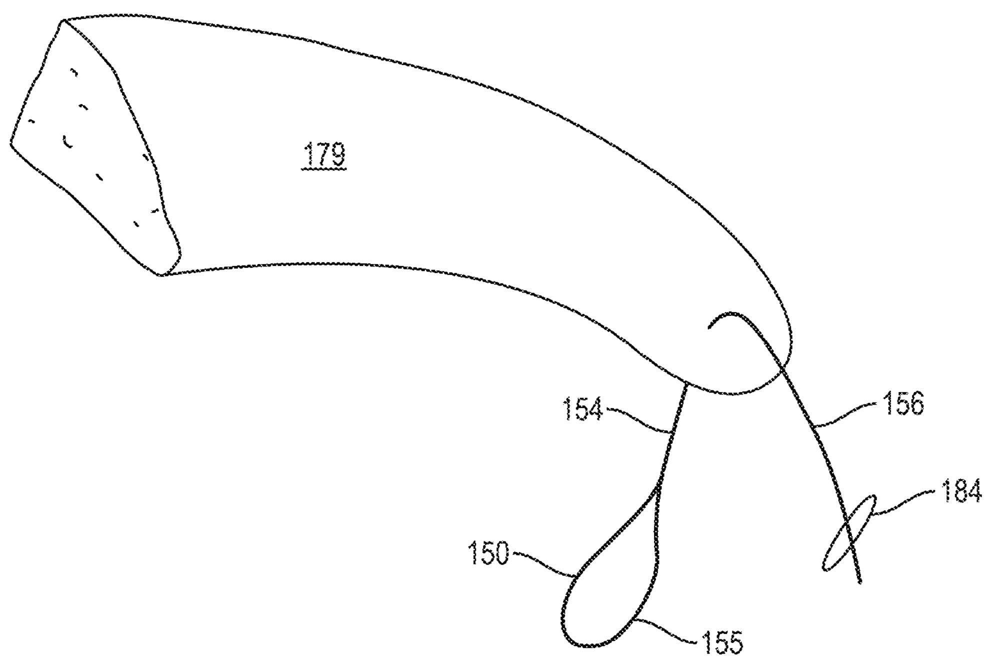

FIGS. 6A-F illustrate an alternative example of a meniscal root repair without use of the anchors 130, 132. As shown in FIG. 6A, the surgeon may then drill one or more bone tunnels 172 through the tibia 174 toward the inferior surface 180 of the meniscus 179. After making a skin portal 184, the surgeon may then insert a delivery tube 186 through the portal 184 and through the meniscus 179 from the superior surface 178 to the inferior surface 180 adjacent a tear in the meniscus (not shown). As shown in FIG. 6B, the surgeon may then insert the looped portion 155 of the suture 150 through the delivery tube 186 such that it exits from the inferior surface 180 of the meniscus 179. The disclosure also contemplates that the suture 150 can be reversed and the non-looped end passed through the delivery tube 186 first. As shown in FIG. 6C, the surgeon may then remove the delivery tube 186, leaving the suture 150 passed through the meniscus 179. The suture 150 may include the round distal portion 154 forming the looped portion 155 and the flat proximal portion 156 passing through the meniscus 179 where it may beneficially impede laceration of the surrounding tissue when tensioned during the tissue repair.

Figure 6D:
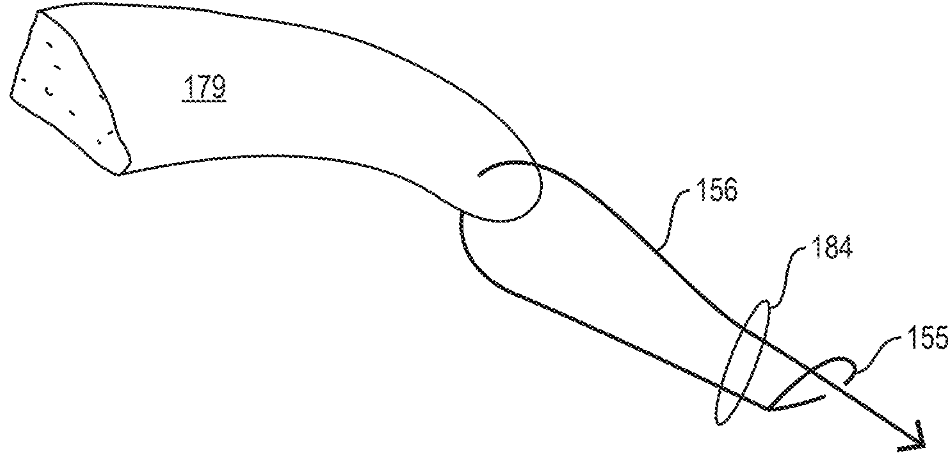
Figure 6E:
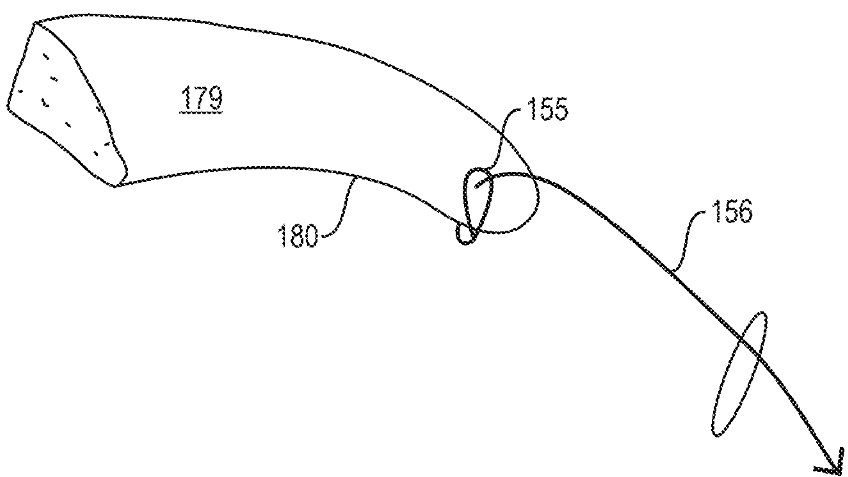
Figure 6F:
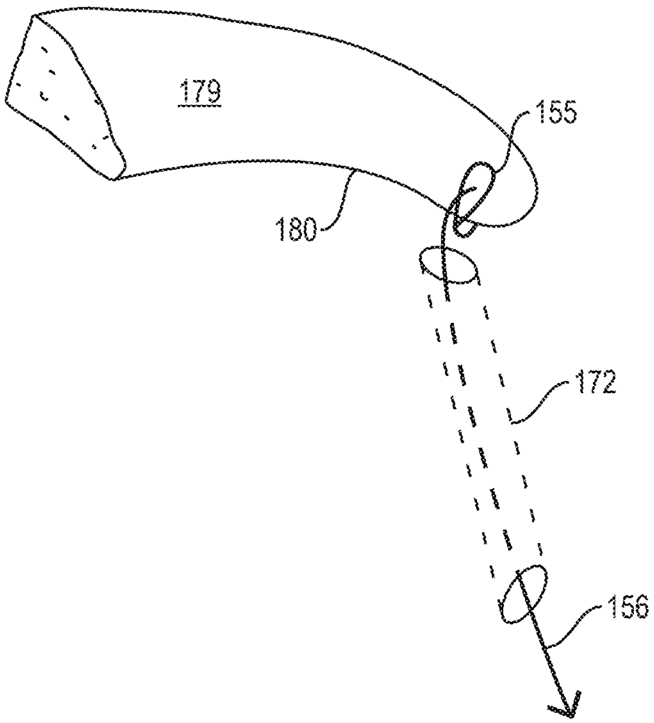

As shown in FIG. 6D, the surgeon may then pass the flat proximal portion 156 through the looped portion 155. As shown in FIG. 6E, the surgeon may then tension the flat proximal portion 156 such that the looped portion 155 is secured to the inferior surface 180 of the meniscus 179. As shown in FIG. 6F, the surgeon may then pull the flat proximal portion 156 through the bone tunnel 172 and secure the flat proximal portion 156 to the tibia 174 as described above.

While the disclosure particularly shows and describes preferred examples, those skilled in the art will understand that various changes in form and details may exist without departing from the spirit and scope of the present application as defined by the appended claims. The scope of this present application intends to cover such variations. As such, the foregoing description of examples of the present application does not intend to limit the full scope conveyed by the appended claims.

The invention claimed is:

1. A tissue repair device, comprising:

a handle;

an elongated needle defining a bore extending from the handle, the elongated needle including a proximal end and a distal end;

a first anchor disposed at least partially within the bore of the elongated needle, the first anchor defining a U-shaped suture pathway beginning and ending at a top surface of the first anchor;

a second anchor disposed at least partially within the bore of the elongated needle proximal to the first anchor;

a first flexible member, a distal end of the first flexible member comprising a round distal portion coupled to only the first anchor by routing a first free end thereof through the U-shaped suture pathway of the first anchor; and a second flexible member separate from the first flexible member, a distal end of the second flexible member comprising a looped portion coupled to only the second anchor;

wherein, after routing through the U-shaped suture pathway of the first anchor, the first free end of the round distal portion of the first flexible member is further routed through a center of the round distal portion outside of the U-shaped suture pathway, creating a finger trap above the top surface of the first anchor, the first flexible member transitioning from the round distal portion at a first side of the finger trap to a flat proximal portion on a second side of the finger trap opposite the first side.

2. The tissue repair device of claim 1, further comprising:

a knob at least partially disposed within the handle; and a hub coupled to the knob, the hub including a flange for manually advancing the knob over the hub.

3. The tissue repair device of claim 2, wherein the elongated needle extends from the handle through an outer tube extending through the hub.

4. The tissue repair device of claim 1, wherein a distal portion of the elongated needle is curved relative to a proximal portion of the elongated needle.

5. The tissue repair device of claim 1, wherein an outer surface of the elongated needle defines a slot extending from the outer surface to the bore, and wherein an upper surface of the first and second anchors projects above the slot.

6. The tissue repair device of claim 5, wherein a curvature of the elongated needle extends in-line with the slot.

7. The tissue repair device of claim 1, wherein the elongated needle further comprises a beveled, tissue piercing tip.

8. The tissue repair device of claim 1, wherein at least one of the first and second flexible members comprises suture or suture tape.

9. The tissue repair device of claim 1, wherein at least one of the first and second anchors comprises an elongate, generally cylindrical body and a rail extending from a top surface of the body.

10. The tissue repair device of claim 9, wherein at least one end of the rail includes a beveled end sloped toward the top surface of the body.

11. The tissue repair device of claim 1, wherein at least one of the first and second anchors has a symmetrical cross-section along both a length and width of the anchor.

12. A method of tissue repair comprising:

creating at least one bone tunnel through a bone extending toward a tear in tissue;

inserting an elongated needle of a tissue repair device through the at least one bone tunnel, the tissue repair device comprising:

a handle;

the elongated needle defining a bore extending from the handle, the elongated needle including a proximal end and a distal end;

a first anchor disposed at least partially within the bore of the elongated needle, the first anchor defining a U-shaped suture pathway beginning and ending at a top surface of the first anchor;

a second anchor disposed at least partially within the bore of the elongated needle proximal to the first anchor;

a first flexible member, a distal end of the first flexible member comprising a round distal portion coupled to only the first anchor by routing a first free end thereof through the U-shaped suture pathway of the first anchor; and a second flexible member separate from the first flexible member, a distal end of the second flexible member comprising a looped portion coupled to only the second anchor;

wherein, after routing through the U-shaped suture pathway of the first anchor, a first free end of the round distal portion of the first flexible member is further routed through a center of the round distal portion outside of the U-shaped suture pathway, creating a finger trap above the top surface of the first anchor, the first flexible member transitioning from the round distal portion at a first side of the finger trap to a flat proximal portion on a second side of the finger trap opposite the first side; and deploying the first anchor from the bore of the elongated needle on a first side of the tear such that the first flexible member extends through the at least one bone tunnel to an outside surface of the bone.

13. The method of claim 12, further comprising deploying the second anchor from the bore of the elongated needle on a second side of the tear such that the second flexible member extends through the at least one bone tunnel to an outside surface of the bone.

14. The method of claim 13, further comprising securing second free ends of the first and second flexible members to the outside surface of the bone with a fixation device.

* * * * *